United States Patent [19]

Zawodzinski et al.

[11] Patent Number: 5,227,042
[45] Date of Patent: Jul. 13, 1993

[54] CATALYZED ENZYME ELECTRODES

[75] Inventors: Thomas A. Zawodzinski; Mahlon S. Wilson, both of Los Alamos, N. Mex.; Judith Rishpon, Ramat-Aviv, Israel; Shimshon Gottesfeld, Los Alamos, N. Mex.

[73] Assignee: The United States of America as represented by the United States Department of Energy, Washington, D.C.

[21] Appl. No.: 883,746

[22] Filed: May 15, 1992

[51] Int. Cl.$^5$ ............................................. G01N 27/26
[52] U.S. Cl. ................................. 204/403; 204/416; 204/418; 435/288; 435/291; 435/817
[58] Field of Search ........... 204/403, 416, 418, 153.12; 435/817, 174, 177, 288, 291

[56] References Cited

U.S. PATENT DOCUMENTS

| | | | |
|---|---|---|---|
| 4,970,145 | 11/1990 | Bennetto et al. | 435/14 |
| 5,082,550 | 1/1992 | Risphon et al. | 204/403 |
| 5,160,418 | 11/1992 | Mullen | 204/403 |

OTHER PUBLICATIONS

H. P. Bennetto et al., "A Glucose Oxidase Electrode for Amperometric Determination of Glucose," International Industrial Biotechnology #2, pp. 5-10 (Mar.-/Apr. 1988).

Primary Examiner—John Niebling
Assistant Examiner—Bruce F. Bell
Attorney, Agent, or Firm—Ray G. Wilson; Paul D. Gaetjens; William R. Moser

[57] ABSTRACT

An enzyme electrode is prepared with a composite coating on an electrical conductor. The composite coating is formed from a casting solution of a perfluorosulfonic acid polymer, an enzyme, and a carbon supported catalyst. The solution may be cast directly on the conductor surface or may be formed as a membrane and applied to the surface. The perfluorosulfonic acid ionomer formed from the casting solution provides an insoluble biocompatible protective matrix for the enzyme and acts to retain the enzyme for long term availability in the electrode structure. The carbon supported catalyst provides catalytic sites throughout the layer for the oxidation of hydrogen peroxide from the enzyme reactions. The carbon support then provides a conductive path for establishing an electrical signal to the electrical conductor. In one embodiment, the electrical conductor is a carbon cloth that permits oxygen or other gas to be introduced to the perfluorosulfonic polymer to promote the enzyme reaction independent of oxygen in the solution being tested.

12 Claims, 5 Drawing Sheets

CATALYZED ENZYME ELECTRODES

BACKGROUND OF INVENTION

This invention relates to enzyme electrodes and, more particularly, to enzyme electrodes having an electrical response arising from the oxidation of a product of the enzyme reaction.

Enzyme electrodes are amperometric sensors that incorporate an enzyme as a catalyzing element on a conductive electrode surface. In one form of enzyme electrode, an enzyme catalyzes the reaction of a selected material with oxygen to produce a reaction product and hydrogen peroxide. The hydrogen peroxide is then oxidized on a catalytic electrode surface to provide an electrical signal that is functionally related to the quantity of selected material in the sample being analyzed. Suitable catalytic materials include platinum (Pt) and other elements from the platinum group of the Periodic Table. By way of example, various body substances, such as glucose, urea, uric acid, triglycerides, amino acids, lactic acid, etc., react with appropriate enzymes, e.g., glucose oxidase (GO-ase), galactose oxidase, alcohol oxidase, lactic acid oxidase, etc., respectively, to generate hydrogen peroxide.

The usefulness of enzyme electrodes can be greatly increased if the sensitivity of the electrode is increased to enable small quantities of material to be detected and if the reaction time of the electrode can be decreased to enable relatively rapid changes in the material concentration to be detected. It is also desirable for the enzyme to be highly stable on the electrode so that measurements can be continued over long periods of time.

In one approach to improving the response of enzyme electrodes, GO-ase enzymes have been applied to the surface of a catalyzed carbon electrode structure such as conventionally used in gas reaction fuel cells. See, e.g., U.S. Pat. No. 4,979,145, issued Nov. 13, 1990, to Bennetto et al. As described in the '145 patent, conventional fuel cell electrode materials are cleaned, treated with an immobilizing solution, and then immersed in a solution containing the enzyme to immobilize an enzyme on the electrode surface. In one embodiment the enzyme is protected by the application of any overlying porous film. The Pt catalyst loading on the electrode was from 5-15% by weight of the total carbon. A substantial improvement in response time, sensitivity, and stability is reported over conventional enzyme electrodes.

A improvement in providing enzymes on a conductive surface is reported in U.S. Pat. No. 5,082,550, issued Jan. 21, 1992, to Rishpon et al. An enzyme, such as GO-ase, is mixed with a perfluorosulfonic polymer and cast onto a catalytic conductive surface, such as Pt. The perfluorosulfonic polymer is permeable to most fluids of interest while providing an insoluble biocompatible matrix for the enzyme and protecting the enzyme against bacterial degradation in both in-vivo and in-vitro environments. The perfluorosulfonic polymer also dissolves large quantities of oxygen to promote the formation of hydrogen peroxide in a stable manner, while accommodating small scale fluctuations in the level of oxygen of the surrounding medium. Thin films of the cast material are generally desired in order to enhance the sensitivity and speed of response of the resulting enzyme coating. However, one limitation of the enzyme-loaded film is that any hydrogen peroxide that is generated in the film must traverse the film to reach the catalytic electrode surface in order for the signal to be generated.

In view of the above enzyme sensors, it is an object of the present invention to minimize the distance for hydrogen peroxide to travel to reach a catalytic surface.

It is another object of the present invention to provide the enzyme in a matrix that provides access to a selected material to enable a rapid signal production in response to changes in the concentration of the selected material.

Yet another object of the present invention is to maintain a stable oxygen supply about the enzyme to promote the formation of hydrogen peroxide and maintain proportionality between the measured signal and the concentration of the material that is analyzed.

One other object of the present invention is to promote the formation of hydrogen peroxide adjacent an appropriate catalyst for oxidation that produces an electrical signal.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise an enzyme electrode for generating an output signal functionally related to the concentration of a substance acted upon by a selected enzyme to generate hydrogen peroxide. A conductive support surface is provided to support and to electrically connect an enzyme layer to a signal analysis system. The enzyme layer is formed on the conductive support surface and is comprised of a perfluorosulfonic acid polymer, the selected enzyme disposed generally uniformly in the polymer, and particles of carbon supported platinum (Pt/C) disposed in the polymer to catalyze oxidation of the hydrogen peroxide and in a concentration effective to provide a conductive path to the conductive support surface for electrons from the oxidation reaction.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF THE PRESENT INVENTION

In accordance with the present invention, a casting solution of a perfluorosulfonic acid polymer, an enzyme, and a carbon supported catalyst is prepared and coated over an electrical conductor to form a sensor for detecting materials that react with the enzyme to produce hydrogen peroxide. The solution can be cast as a membrane or cast directly on an electrode conductor surface to form a polymeric enzyme immobilization layer without concerns for degrading the enzyme. The perfluorosulfonic acid polymer formed from the casting solution provides an insoluble biocompatible protective matrix for the enzyme and acts to retain the enzyme for long term availability in the electrode structure. The perfluorosulfonic acid polymer also dissolves large quantities of oxygen that is then available adjacent the enzyme to promote hydrogen peroxide formation for signal generation.

The significant advance of the present invention is the inclusion of a carbon supported catalyst within the polymeric enzyme immobilization layer. The catalyst is available near the site of hydrogen peroxide generation for efficient oxidation of the hydrogen peroxide in the reaction

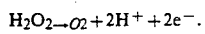

$$H_2O_2 \rightarrow O_2 + 2H^+ + 2e^-.$$

The supporting carbon then forms a conductive path for the resulting electrons to the supporting electrode surface for the resulting signal.

Figures 1A, 1B:
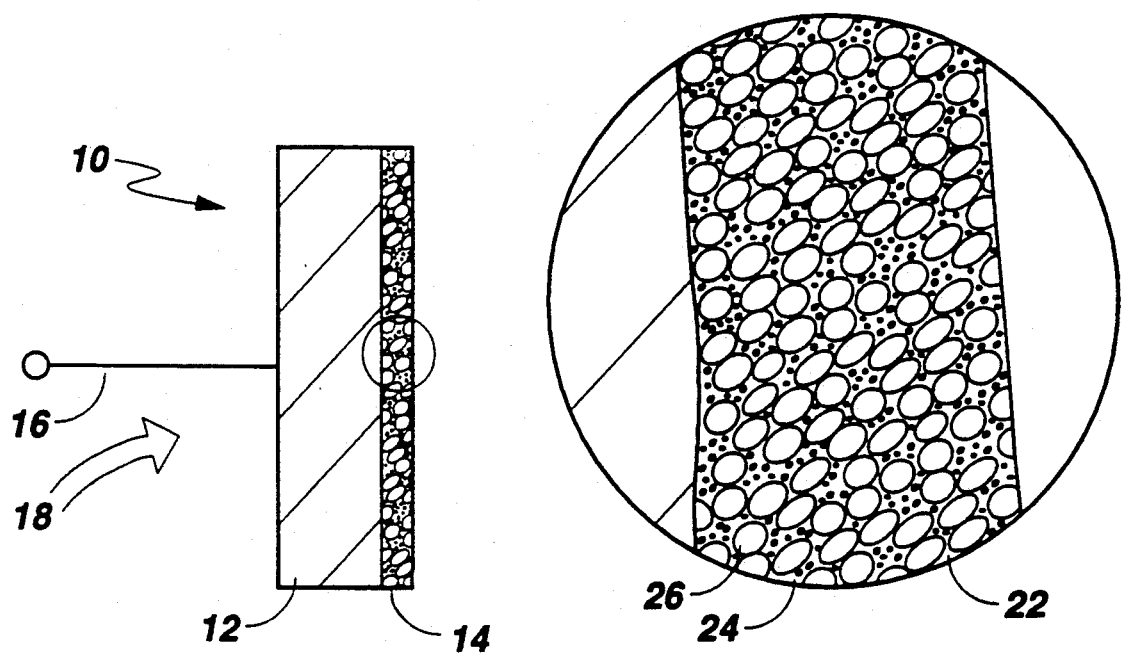
FIG. 1A and 1B are schematic drawings of an enzyme electrode according to the present invention.

FIG. 1 pictorially depicts an enzyme electrode structure 10 according to the present invention. A conductive backing 12 provides support for enzyme coating 14. Output lead 16 electrically connects backing 12 to a suitable signal detection and/or analysis system. Backing 12 is generally an inert conducting structure, i.e., does not have any catalytic activity, and may be formed as a glassy, i.e., vitreous, carbon surface or may be a carbon paper or cloth electrode such as used in fuel cell structures as explained in the '145 patent. Commercial carbon cloth electrodes are available from the Prototech Company of Newton Highlands, Mass., either with or without carbon supported catalyst particles bound to the electrode structure. Carbon paper electrodes are available from Toray of Japan. As used herein, the term "carbon cloth" will be understood to mean either carbon cloth or carbon paper electrode backings. In one advantageous embodiment of the invention, conductive backing 12 is a porous carbon cloth structure with the uncoated side open to a supply of air or oxygen 18 to obviate the need for oxygen in the solution being measured, where the air/oxygen can permeate the backing structure and is dissolvable by the perfluorosulfonic acid polymer.

Enzyme-containing coating 14 is formed to (a) provide a supporting and protective polymer structure 22 for a selected enzyme 24 where the supporting structure is permeable to a substance to be detected; (b) provide a catalyst 26 in close proximity to the enzyme reaction that produces $H_2O_2$ to catalyze the oxidation of the $H_2O_2$; and (c) provide a conductive path to conductive support structure 12 for electrons produced by the oxidation reaction. A perfluorosulfonic acid polymer is preferably used to form a protective support structure 22. These polymers act as a solute for oxygen to provide an oxygen source for the enzyme reaction, ion conductivity for charge transport, and a binder for the composite structure. As discussed above, a suitable enzyme 24 is selected to react with a corresponding material to produce $H_2O_2$. The catalytic surface for $H_2O_2$ electrooxidation is provided by carbon supported catalyst particles 26 that are dispersed throughout polymer 22 in close proximity to the sites of $H_2O_2$ production that are catalyzed by enzymes 24. The carbon support for the catalyst also provides an electrically conductive path for electrons produced by the oxidation reaction. The electrons are transported to an adjacent carbon particle and through a resulting conductive path to the surface of electrode 12.

Suitable perfluorosulfonic acid polymers are commercially available as Nafion (a registered trademark of Du Pont Company), membrane "C" (Chlorine Engineers, Inc. of Japan), and Dow membrane (Dow Chemical Company). The dissolved form of the polymer may also be obtained and used to form the ionic polymer. For example, a 5% solution by weight of Nafion (polymer) in an alcohol/water mixture is available from Solution Technologies.

Many commercial forms of carbon supported catalyst are available with different catalysts from the platinum group and different catalyst loadings on the carbon particles. The examples herein use about 10% by weight of Pt on XC-72 carbon particles (Prototech) (C/Pt), but the invention is certainly not limited to this particular form of carbon supported catalyst. Other catalysts from the Pt group, such as palladium, ruthenium, or rhodium, could be used in place of Pt.

The following examples illustrate the need for each of the above components in the enzyme layer.

Electrode A—No C/Pt: 2.5 ml of 0.5% by weight of Nafion in commercial alcohol solution and buffered to about pH 7 was mixed with 5 μl of a 100 mg/ml solution of GO-ase in phosphate buffer (PB). 10 μl of this solution was cast onto a glassy carbon (GC) electrode having an area of 0.07 cm². The electrode was not active. (N.B. the same solution on a Pt electrode did respond to glucose.

Electrode B—No Pt: 2 mg of polyvinylpyrrolidinone (PVP) and 20 mg of colloidal graphite (Cabot) without Pt was suspended in 1 ml of isopropanol; 100 μl of 0.5% Nafion suspension prepared as in Electrode A was applied to a GC electrode. The electrode was not active. The electrode became active, however, in the presence of p-benzoquinone, indicating that the enzymatic function was preserved but, in the absence of Pt, a redox mediator was necessary (poor electrocatalysis of $H_2O_2$ oxidation at the GC electrode).

Electrode C—No Nafion: 2 mg of PVP and 20 mg of C/Pt (Prototech) was suspended in 1 ml of isopropanol; 100 μl of this suspension was mixed with 20 μl of GO-ase (100 mg/ml); 10 μl of the resulting solution was applied to a GC electrode. The electrode was active (50 μA maximum current) but not mechanically stable, i.e., the active layer began to peel off the electrode. Addition of a Nafion overlayer did not stabilize the electrode.

Electrode D: 2 mg of PVP and 20 mg of C/Pt (Prototech) was suspended in 1 ml of isopropanol plus 200 μl of 5% Nafion solution in mixed alcohols; 100 μl of suspension was mixed with 20 μl of GO-ase (100 mg/ml); 10 μl of the resulting suspension was applied to a GC electrode. On the third day of testing 5 mA/cm² maximum current was obtained. By the fourth day, about 25% of the initial activity had been lost. The electrode has been subsequently stable for more than 130 days.

Figure 2:
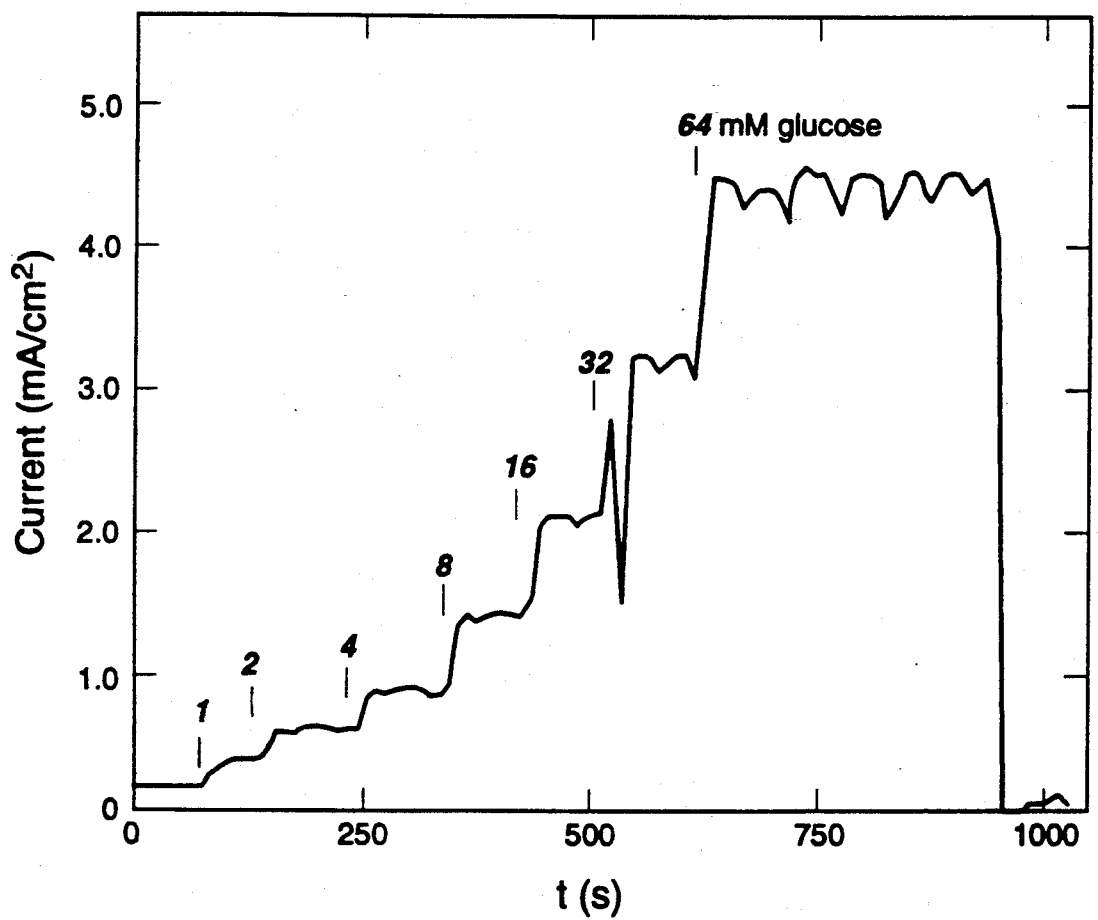
FIG. 2 graphically depicts the output signal strength response time of an enzyme electrode according to the present invention.

FIG. 2 graphically depicts the response to successive glucose additions of an enzyme electrode fabricated in accordance with Example D., above. By way of comparison with an enzyme structure taught by the '550 patent, supra, i.e., an enzyme/Nafion layer on a smooth Pt electrode, the response time of the enzyme layer to successive glucose additions is rapid in both cases, about 2-4 seconds. The magnitude of the response with C/Pt particles dispersed in the Nafion layer with the enzyme is, however, about 4.3 mA/cm$^2$ for a glucose concentration of 113 mM compared with only 6.5 $\mu$A/cm$^2$ for the '550 configuration. The present configuration also provides significantly lower noise levels due to fluctuations in flow caused by solution stirring.

Figure 3:
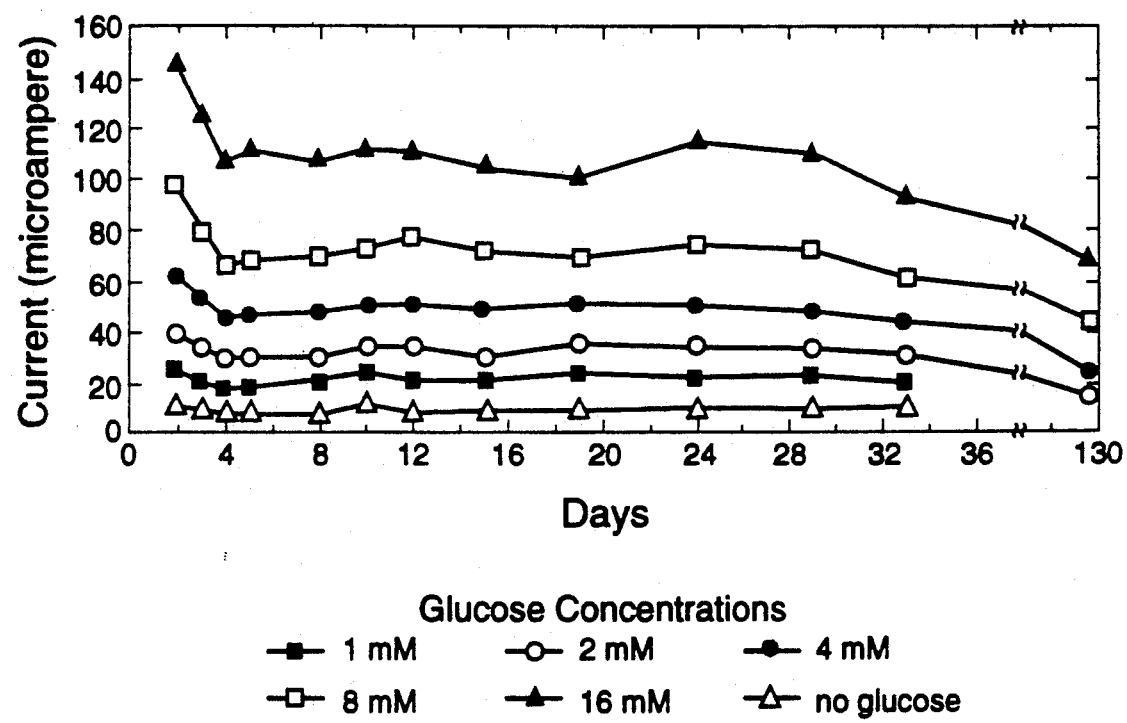
FIG. 3 graphically depicts the long term stability of an enzyme electrode according to the present invention.

FIG. 3 illustrates the stability of the present electrode at a variety of glucose concentrations. After an initial signal decrease of about 25% over the first four days, the output is relatively stable for a long period. Even after 130 days, significant output remains, although the response has decreased somewhat.

The composition of the enzyme layer has been varied to incorporate varying amounts of C/Pt and the response to a solution containing 113 mM glucose was measured. As shown in Table B, the primary factor influencing the signal strength is the fractional amount of C/Pt in the layer.

TABLE B

| | ENZYME LAYER COMPOSITIONS | | | |
|---|---|---|---|---|
| | Nafion ($\mu$g) | Enzyme ($\mu$g) | C/Pt ($\mu$g) | Max Current ($\mu$A) |
| 1 | 37 | 170 | 152 | 80 |
| 2 | 69 | 170 | 139 | 175 |
| 3 | 138 | 170 | 111 | 250 |
| 4 | 208 | 170 | 83 | 100 |
| 5 | 278 | 170 | 56 | 0 |

Electrodes were 0.07 cm$^2$ glassy carbon area; enzyme was GO-ase; and sample contained 113 mM glucose. C/Pt particles contain 10% Pt by weight.

Figure 4:
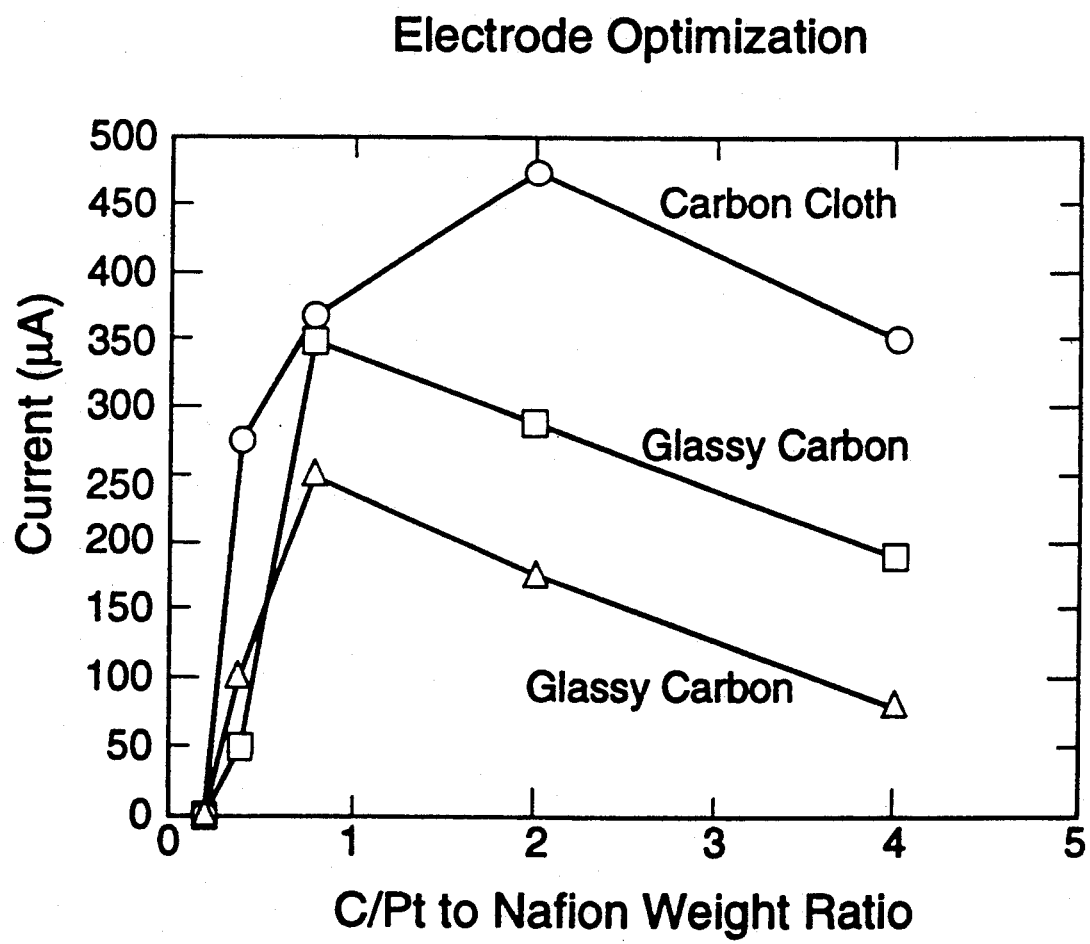
FIG. 4 graphically depicts the functional relationship between sensor response current and C/Pt loadings.

FIG. 4 graphically shows the functional relationship between fractional C/Pt loading in the enzyme film and the output current. An enzyme loading of 170 $\mu$g per electrode was used to sense a glucose solution with a concentration of 113 mM glucose. It is apparent that a minimum concentration of C/Pt is required to establish the necessary electrically conductive path for electrons arising from the oxidation of the H$_2$O$_2$.

It has also been found in accordance with the present invention, as shown in FIG. 4, that an optimum (C/Pt)/Nafion ratio can be found to maximize the output current. The optimum ratio is a function of the carbon electrode type, e.g., GC or carbon cloth; the relative weights of C and Pt in the C/Pt catalyst, the enzyme loading, the enzyme layer thickness, etc., and can readily be determined once the design parameters are finalized. It has also been found that optimum electrode performance was obtained at an enzyme-to-Nafion weight ratio of about four (4).

In a particularly advantageous embodiment, discussed above with reference to FIG. 1, electrode 12 is formed of a porous carbon paper so that a gas 18 can be introduced through the electrode structure 12 to enzyme layer 14. In one application, a sensor with an open electrode structure and an air/oxygen supply can be used with solutions that have no dissolved oxygen. Oxygen is supplied by air/oxygen supply 18 through the back side of the electrode to dissolve in the perfluorosulfonate acid polymer 22 and to promote the enzyme reaction with a material in solution to form H$_2$O$_2$.

Figure 5:
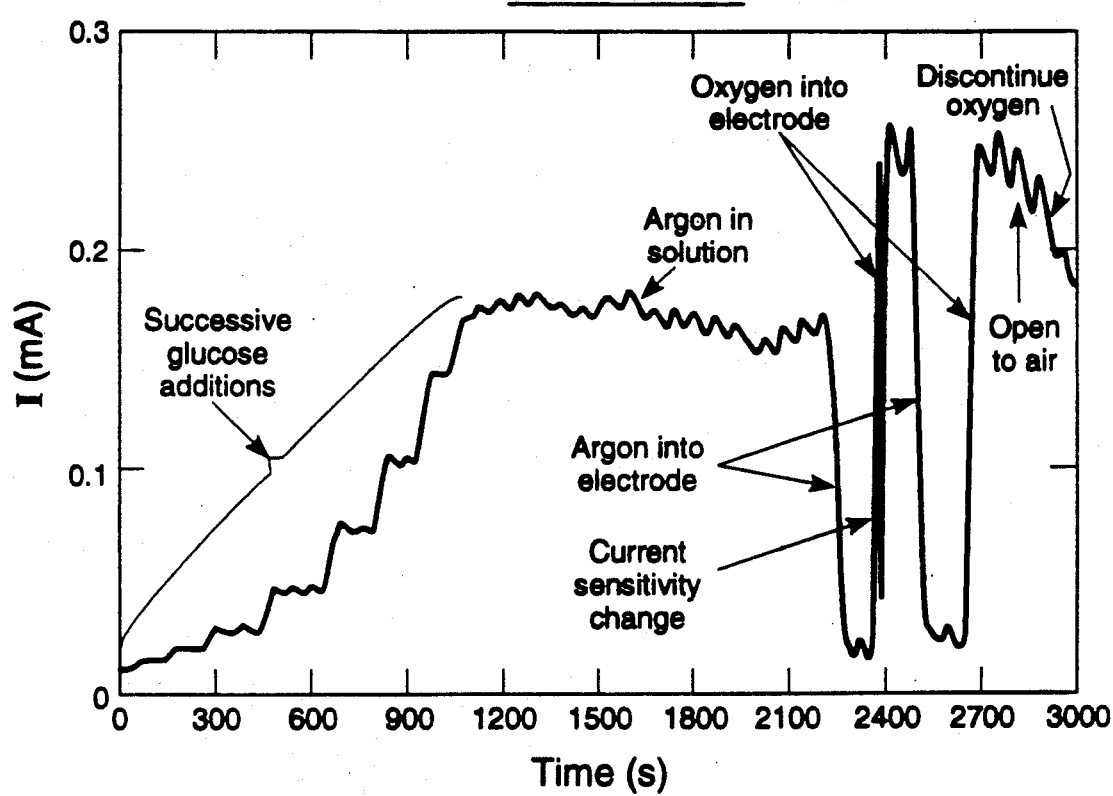
FIG. 5 graphically depicts the sensitivity of the enzyme electrode to gases introduced directly into the solution containing the material to be analyzed or through a porous carbon paper backing.

FIG. 5 graphically depicts the response of a carbon cloth electrode structure with an enzyme layer having a composition identical to that shown for Electrode D. Glucose is added incrementally to a solution having dissolved oxygen and oxygen is also supplied to the perfluorosulfonate acid polymer material by opening the backside of the carbon paper electrode to air. The oxygen in the solution was first replaced with argon and oxygen was supplied solely by air diffusing through the back of the porous electrode. No substantial change in performance is observed as shown in FIG. 5.

The oxygen supply through the electrode was then replaced with argon. With argon in the solution and argon supplied through the porous backing, the electrode response was killed since there was no longer any oxygen to support the enzyme reaction. The argon at the back of the electrode was again replaced with oxygen and the electrode response was renewed. The use of oxygen rather than air provided an enhanced response over that obtained with air. Thus, the porous carbon backing provides a capability that is not available with solid electrodes. For example, a small sensor could be placed within a needle where the enzyme layer is open to the sample to be tested and the conductive backing is open to air or oxygen through the needle.

It will be understood that the porous electrode structure open to a gas flow broadens the applications of the enzyme electrode to include the sensing of gas streams containing materials that are suitable for enzyme reactions, such as some air contaminants. The perfluorosulfonate acid polymer must be kept moist, but the sample gas and oxygen, if necessary, can be introduced through the porous electrode.

The foregoing description of embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An enzyme electrode for generating an output signal functionally related to the concentration of a substance acted upon by a selected enzyme to generate hydrogen peroxide, comprising:
   a conductive support surface; and
   an enzyme layer formed on said surface, said enzyme layer comprised of a perfluorosulfonic acid polymer, said selected enzyme, and particles of carbon supported catalyst selected from the platinum group disposed in said polymer to catalyze oxidation of said hydrogen peroxide and in a concentration effective to provide a conductive path to said conductive support surface for electrons from said oxidation reaction.

2. An enzyme electrode according to claim 1, wherein said catalyst is selected from the platinum group consisting of platinum, palladium, ruthenium, and rhodium.

3. An enzyme electrode according to claim 1, wherein said conductive support surface is glassy carbon.

4. An enzyme electrode according to claim 1, wherein said conductive support surface is a gas transmissive carbon cloth.

5. An enzyme electrode according to claim 2, wherein said conductive support surface is a gas transmissive carbon cloth.

6. An enzyme electrode according to claim 1, wherein said catalyst is platinum.

7. An enzyme electrode according to claim 1, wherein said enzyme is selected from the group consisting of glucose oxidase, galactose oxidase, alcohol oxidase, lactic acid oxidase, amino acid oxidase, and cholesterol oxidase.

8. An enzyme electrode according to claim 5, wherein said carbon paper has a second surface open to a gas supply.

9. An enzyme electrode according to claim 8, where said gas supply contains oxygen.

10. In an enzyme electrode for generating an output signal functionally related to the concentration of a substance acted upon by a selected enzyme to generate hydrogen peroxide, where an enzyme layer is formed on a conductive support surface, an improved enzyme layer consisting of:
a perfluorosulfonic acid polymer, said selected enzyme, and particles of carbon supported catalyst selected from the platinum group disposed in said polymer to catalyze oxidation of said hydrogen peroxide and provide a conductive path to said conductive support surface for electrons from said oxidation reaction.

11. An enzyme electrode according to claim 10, wherein said conductive support surface is a gas transmissive carbon cloth.

12. An enzyme electrode according to claim 12, wherein said catalyst is platinum.

* * * * *